United States Patent [19]

Dessau

[11] Patent Number: 5,284,986
[45] Date of Patent: Feb. 8, 1994

[54] UPGRADING OF NORMAL PENTANE TO CYCLOPENTENE

[75] Inventor: Ralph M. Dessau, Edison, N.J.

[73] Assignee: Mobil Oil Corporation, Fairfax, Va.

[21] Appl. No.: 966,656

[22] Filed: Oct. 26, 1992

Related U.S. Application Data

[60] Continuation-in-part of Ser. No. 878,267, May 4, 1992, which is a continuation-in-part of Ser. No. 418,377, Oct. 6, 1989, Pat. No. 5,192,728, which is a division of Ser. No. 211,198, Jun. 24, 1988, Pat. No. 4,990,710.

[51] Int. Cl.$^5$ ............................................. C07C 5/327
[52] U.S. Cl. ................................... 585/318; 585/311; 585/313; 585/317; 585/365; 585/379
[58] Field of Search .............. 585/258, 259, 260, 365, 585/419, 420, 324, 310, 313, 317, 318, 379

[56] References Cited

U.S. PATENT DOCUMENTS

| | | | |
|---|---|---|---|
| Re. 29,948 | 3/1979 | Dwyer et al. | 208/110 |
| 3,702,293 | 11/1972 | Hayes et al. | 208/139 |
| 3,702,294 | 11/1972 | Rausch | 208/139 |
| 3,878,131 | 4/1975 | Hayes | 252/466 PT |
| 4,104,320 | 8/1978 | Bernard et al. | 260/673.5 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,416,806 | 11/1983 | Bernard et al. | 502/74 |
| 4,418,006 | 11/1983 | Kim et al. | 502/73 |
| 4,435,283 | 3/1984 | Buss et al. | 208/138 |
| 4,456,527 | 6/1984 | Buss et al. | 208/89 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,547,472 | 10/1985 | Van Nordstrand | 502/66 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/66 |
| 4,830,729 | 5/1989 | Dessau et al. | 208/89 |
| 4,849,567 | 7/1989 | Dessau et al. | 585/379 |
| 4,851,599 | 7/1989 | Dessau | 585/407 |
| 4,868,145 | 9/1989 | Dessau et al. | 502/66 |
| 4,882,040 | 11/1989 | Dessau et al. | 208/138 |
| 4,886,926 | 12/1989 | Dessau et al. | 585/444 |
| 4,892,645 | 1/1990 | Dessau | 208/111 |
| 4,910,357 | 3/1990 | Dessau et al. | 585/322 |
| 4,935,566 | 6/1990 | Dessau et al. | 208/65 |
| 4,990,710 | 2/1991 | Dessau et al. | 585/277 |
| 5,037,529 | 8/1991 | Dessau et al. | 208/64 |
| 5,103,066 | 4/1992 | Dessau | 568/406 |
| 5,122,489 | 6/1992 | Dessau | 502/66 |
| 5,124,497 | 6/1992 | Dessau et al. | 585/419 |

FOREIGN PATENT DOCUMENTS 2033358A  5/1980  United Kingdom.

OTHER PUBLICATIONS

Thomas, C. L., Catalytic Processes and Proven Catalysts, New York: Academic Press, 120-123 (1970).
Dragutan, V., et al., Olefin Metathesis and Ring-Opening Polymerization of Cyclo-Olefins, New York: John Wiley & Sons, Ltd., 160-164 (1985).

*Primary Examiner*—Asok Pal
*Assistant Examiner*—P. Achutamurthy
*Attorney, Agent, or Firm*—Alexander J. McKillop; Dennis P. Santini; Lori F. Cuomo

[57] ABSTRACT

This invention is a process of converting n-pentane to cyclopentene. In accordance with a preferred embodiment n-pentane feed is converted in a dual temperature stage-dual catalyst process without interstage processing of the first-stage product mixture.

27 Claims, No Drawings

UPGRADING OF NORMAL PENTANE TO CYCLOPENTENE

CROSS-REFERENCE TO RELATED APPLICATION

This application is a continuation in part of copending Ser. No. 07/878,267, filed May 4, 1992, which is a continuation of Ser. No. 07/418,377, now U.S. Pat. No. 5,192,728, filed Oct. 6, 1989 which is a division of Ser. No. 07/211,198, filed Jun. 24, 1988 now U.S. Pat. No. 4,990,710.

FIELD OF THE INVENTION

The process of the invention relates to a dual stage process for conversion of n-pentane to cyclopentene. The conversion is conducted catalytically in a dual stage-dual catalyst process.

BACKGROUND OF THE INVENTION

With the increase in cracking severity of FCC and the rise of hydroprocessing, the problem of processing byproduct n-pentane has become more significant. Some refineries isomerize the low 61.7 RON (research octane number) n-pentane to isopentane (RON=92.3). Isomerization of the n-pentane to isopentane leads, however, to an increase in gasoline volatility (RVP of n-pentane=15.6; RVP of isopentane=20.4); and environmental factors may limit the amount of isopentane usable in gasoline in the future.

Cyclopentene offers several advantages over n-pentane as a gasoline additive. Its research octane number is higher and its volatility is substantially lower, as shown below:

| Compound | RON | MON | BP (°F.) |
|---|---|---|---|
| n-pentane | 61.7 | 62.6 | 97 |
| cyclopentene | 93.3 | 69.7 | 112 |

Cyclopentene can also be converted to cyclopentanol or cyclopentyl methyl ether for octane boosting. Cyclopentene is also an important monomer. V. Dragutan et al., *Olefin Metathesis and Ring Opening Polymerization of Cycloolefins* 160–163 (1985), incorporated herein by reference.

Therefore, it is an object of the present invention to provide a process for upgrading the poor octane n-pentane component of gasoline. It is a further object of the present invention to provide a product stream rich in cyclopentene.

SUMMARY OF THE INVENTION

The process of the invention relates to catalytic conversion of n-pentane to cyclopentene in a dual temperature stage process. The catalyst in the first stage is a Group VIII or VIA metal-containing non-acidic catalyst composition. The catalyst in the second stage is a palladium-containing non-acidic catalyst composition.

In accordance with the invention, the first-stage product mixture is passed over the palladium catalyst at a lower temperature, to produce enhanced yields of cyclopentene. In accordance with the invention, the product mixture of the first stage is subjected to the second-stage temperature conditions without interstage processing of the product resulting from the first stage.

DETAILED DESCRIPTION OF THE INVENTION

Normal pentane is converted to cyclopentene via a dual stage process. In the first stage, n-pentane is dehydrogenated and dehydrocyclized to a mixture of paraffins, naphthenes, olefins and dienes. The effluent from the first stage is then passed over a palladium catalyst at lower temperatures where dienes, especially cyclopentadiene, are rehydrogenated to olefins with the hydrogen coproduced in the first stage.

Palladium catalysts are used to selectively saturate dienes to olefins and leave olefins intact. C.L. Thomas, *Catalytic Processes and Proven Catalysts* 120–123 (1970), incorporated herein by reference.

First-Stage Process Conditions

In accordance with the invention, the first stage comprises contacting a feed comprising n-pentane, with a Group VIII metal or Group VIA metal containing non-acidic catalyst composition.

In accordance with the invention, the first stage of the catalytic process is conducted at elevated temperatures ranging from 300° C. to 700° C., and, preferably from 400° C. to 600° C., and most preferably at a temperature ranging from 450°–600° C. In the first stage, pressure conditions include pressures varying from subatmospheric, to atmospheric to greater than atmospheric. Preferred pressures range from 0.1 atmospheres to atmospheric. However, pressures up to 100 psig can be employed. The weight hourly space velocity ranges from 0.02 to 50 hr$^{-1}$, preferably from 0.1 to 10 hr$^{-1}$.

The first stage may be conducted in the presence or absence of purposefully added hydrogen and preferably, in the presence of diluents inert to conditions of the catalytic dehydrogenation such as nitrogen and methane, and aromatics including $C_6$–$C_8$ aromatics (benzene, toluene, xylene(s) including the o-, m- and p-isomers). In particular, the first stage can be advantageously conducted in the absence of added hydrogen.

Second-Stage Process Conditions

Accordingly, the second stage of the process comprises subjecting the product effluent of the first stage, to the second-stage conditions.

In accordance with the invention, the second-stage catalysis comprises contacting a feed comprising the product effluent of the first stage with a palladium-containing non-acidic catalyst composition, to produce cyclopentene.

The second stage of the process is conducted at temperatures lower than the temperature in the first stage of the process. In accordance with the invention, catalytic conditions in the second stage include pressures varying from subatmospheric, to atmospheric to greater than atmospheric. Preferred pressures range from 0.1 atmospheres to atmospheric. However, pressures up to 100 psig can be employed. The second stage of the process of the invention is conducted at temperatures ranging up to less than about 300° C., typically from at least 25°–250° C.

The weight hourly space velocity will range from 0.02 to 50 hr$^{-1}$, preferably 0.1 to 10 hr$^{-1}$.

Although the product mixture effluent resulting from the first-stage catalysis can be subjected to interstage processing prior to introduction to the second stage of the process, preferably the product mixture resulting from the first stage is not subjected to interstage processing prior to introduction to the second stage of the process. In a preferred embodiment, the two stages are conducted in a cascade operation. The catalytic stages of the process of the invention can be undertaken in fixed bed, moving bed and/or fluidized bed reactor.

As a result of the two stage catalysis, cyclopentene is produced. Preferably the process of the present invention results in greater than about a 20% yield of cyclopentene and more preferably greater than about 50% yield of cyclopentene.

The Catalysts

Another aspect of the invention is the first- and second-stage catalyst. The first-stage catalyst comprises a Group VIA or a Group VIII metal and a non-acidic microporous material. The second-stage catalyst further comprises palladium as the group VIA or VIII metal. The non-acidic microporous material can also be "crystalline" in the sense that it has a unique X-ray diffraction pattern. Preferably, the microporous crystalline material contains a modifier selected from the group consisting of tin, indium, thallium, lead, gallium and sulfur. The preferred catalysts are described in allowed U.S. patent application Ser. No. 418,377, filed Oct. 6, 1989, and its parent, U.S. Pat. No. 4,990,710, each of Which is relied upon and incorporated by reference herein.

The amount of Group VIII and Group VIA metal in the non-acidic catalyst composition employed in the first stage can range from 0.05 to 10 weight percent and preferably 0.1 to 5 weight percent of the microporous material. In a preferred embodiment, platinum is the Group VIII metal in the first-stage non-acidic catalyst composition. However, the metal can be any Group VIII metal including those of the platinum group (platinum, iridium, and palladium), and chromium.

The amount of palladium in the non-acidic catalyst composition employed in the second stage can range from 0.05 to 10 weight percent and preferably 0.1 to 5 weight percent of the microporous material.

The modifier content of the crystalline microporous materials can range from 0.01 to 20 weight percent. Practically, the modifier content will range from 0.1 to 10 weight percent.

The crystalline microporous materials of the invention can be zeolites characterized by Si/Al ratios of at least 2. However, the silica:alumina ratio of the zeolite can be up to 1000, or greater. In a preferred embodiment the aluminum content of these materials is less than 0.1 weight percent and more preferably less than 0.02 weight percent.

The compositions comprising Group VIA and/or Group VIII metal-containing catalysts do not exhibit any appreciable acid activity. These catalysts would meet the criteria of non-acidic catalysts described by Davis et al., *J. Catal.*, 15, 363 (1969). Thus, a non-equilibrium mixture of xylenes are formed from either n-octane or each individual methylheptane isomer, with the n-octane yielding more o-xylene and 2-methyl-heptane yielding mostly m-xylene, at conversions between 10 and 60%.

The crystalline microporous material has an X-ray diffraction pattern which corresponds to a zeolite, SAPO, ALPO, etc. The preferred microporous crystalline materials are crystalline in the sense that they are identifiable as isostructural with zeolites by X-ray powder diffraction pattern. Preferred zeolites are those having the structure of ZSM-5 and MCM-22.

In a preferred embodiment the pore size of the microporous crystalline silicates ranges from about 5 to about 8 Angstroms. In a preferred embodiment the microporous crystalline material exhibits the structure of ZSM-5, by X-ray diffraction pattern. The X-ray diffraction pattern of ZSM-5 has been described in U.S. Pat. No. 3,702,886 and RE 29,948 each of which is incorporated by reference herein. The zeolite may alternatively be one having the structure of ZSM-11, ZSM-12, ZSM-22, ZSM-23, ZSM-35, MCM-22, or PSH-3. The microporous crystalline material can be MCM-22 which is the subject of U.S. Pat. No. 4,954,325 which is relied upon and incorporated by reference herein.

When, as in embodiments herein, the crystalline material exhibits an X-ray diffraction pattern of a zeolite, at least some of the dehydrogenation metal may be intrazeolitic, that is, some of that metal is within the pore structure of the crystal, although some of that metal can be on the surface of the crystal. A test for determining whether, for example, Pt is intrazeolitic or extrazeolitic in the case of ZSM-5 is reported by R M. Dessau, *J. Catal.* 89, 520 (1984). The test is based on the selective hydrogenation of olefins.

The methods of synthesizing these preferred materials are described in U. S. Pat. No. 4,990,710 which is relied upon and incorporated by reference herein.

The non-acidic, crystalline, microporous, Group VIA and Group VIII metal containing materials used in the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder) and material of the invention. The relative proportions of finely divided crystalline material and inorganic oxide gel matrix vary widely, with the crystal content ranging from about 1 to about 90 percent by weight and more usually, particularly when the composite is prepared in the form of beads, in the range of about 2 to about 80 weight percent of the composite. When used with a matrix or binder, the catalyst of the invention will preferably be combined with non-acidic matrix or binder materials. A preferred matrix or binder material would be silica or titania.

The catalysts may be regenerated by conventional techniques including high pressure hydrogen treatment and combustion of coke on the catalyst with an oxygen-containing gas.

The following example illustrates the process of the present invention.

EXAMPLE n-Pentane dehydrocyclization was conducted in a dual stage reactor. The reaction was conducted in a down-flow $\frac{3}{8}''$ steel reactor containing 1.0 g 0.5% Pt/Sn-ZSM-5 in the first stage, and 0.5 g 0.4% Pd/Sn-ZSM-5 as the catalyst in the second stage.

n-Pentane having a purity >99.4% was introduced into the reactor diluted with nitrogen, with $N_2/C_5=3$, and an $N_2$ flow rate of 6 cc/min. The temperature of the first stage was maintained at 575° C. and the temperature of the second stage was maintained at about 45° C. On-line GC analysis of the reactor effluent showed 94.8% conversion of n-pentane, with the formation of cyclopentene in 52.0% yield, with a selectivity of 54.9%. In addition, 11.5 wt. % cyclopentane was observed. The composition of the complete product stream is shown in Table 1 below:

TABLE 1

| Product Composition of Second Stage Pd Reactor | |
|---|---|
| Product | Wt. % |
| $C_4^-$ paraffins | 9.3 |
| $C_3$, $C_4$ olefins | 3.2 |
| n-pentane | 5.2 |
| iso-pentane | 1.3 |
| n-Pentenes | 10.8 |
| iso-Pentenes | 5.6 |
| cyclopentane | 11.5 |
| Cyclopentene | 52.0 |
| benzene | 1.1 |

Changes and modifications in the specifically described embodiments can be carried out without departing from the scope of the invention which is intended to be limited only by the scope of the appended claims.

What is claimed is:

1. A process for converting n-pentane to cyclopentene comprising:
    contacting n-pentane with a first-stage catalyst bed in which the first catalyst comprises a Group VIA or Group VIII metal and a non-acidic microporous material, wherein the amount of Group VIA or Group VIII metal in the first catalyst is in the range of from about 0.05 to 10 weight percent, at a temperature in the range of from about 300 to about 700° C. to form a first-stage product effluent;
    passing the first-stage product effluent over a second-stage catalyst bed maintained under a second set of conditions in which the temperature is less than about 300° C., wherein the second-stage catalyst bed comprises a second catalyst which second catalyst comprises palladium and a non-acidic microporous material, wherein the amount of palladium in the second catalyst is in the range of from about 0.05 to about 10 weight percent; and
    recovering a second-stage product which comprises cyclopentene.

2. The process of claim 1, wherein the non-acidic microporous material comprises a non-acidic crystalline microporous material.

3. The process of claim 1, wherein the non-acidic microporous material contains a modifier selected from the group consisting of tin, indium, gallium, lead, thallium and sulfur, wherein the modifier content of the crystalline microporous material is in the range of from about 0.01 to about 20 weight percent.

4. The process of claim 1, wherein the non-acidic microporous material exhibits the X-ray diffraction pattern of a zeolite.

5. The process of claim 3, wherein the non-acidic microporous material exhibits the X-ray diffraction pattern of a zeolite.

6. The process of claim 4, wherein the zeolite has the structure of ZSM-5.

7. The process of claim 5, wherein the zeolite has the structure of ZSM-5.

8. The process of claim 4, wherein the zeolite is selected from the group consisting of a zeolite having the structure of ZSM-5, ZSM-11, ZSM-12. ZSM-22, ZSM-23, ZSM-35, MCM-22, and PSH-3.

9. The process of claim 5, wherein the zeolite is selected from the group consisting of a zeolite having the structure of ZSM-5, ZSM-11, ZSM-12, ZSM-22, ZSM-23, ZSM-35, MCM-22, and PSH-3.

10. The process of claim 5, wherein the first-stage temperature is in the range of from about 300° to about 600° C.

11. The process of claim 10, wherein the first-stage temperature is in the range of from about 450 ° to about 600° C.

12. The process of claim 11, wherein the second-stage temperature is in the range of from about 200° to about 300° C.

13. The process of claim 11, wherein the second-stage temperature is in the range of from about 25° to about 250° C.

14. The process of claim 1, wherein the first and second stages are undertaken in a cascade operation without interstage processing of the first-stage product effluent.

15. The process of claim 1, which further includes cofeeding an inert diluent with said n-pentane.

16. The process of claim 15, wherein said diluent is nitrogen, methane or aromatic compounds, and admixtures thereof.

17. The process of claim 16, wherein the diluent is selected from the group consisting of $C_6$-$C_8$ aromatics and admixtures thereof.

18. A process for converting a n-pentane-containing feed to a cyclopentene-enriched product exhibiting research octane number (RON) greater than that of the feed comprising:
    contacting said n-pentane-containing feed with a first-stage catalyst bed in which the first catalyst comprises a metal selected from the group consisting of Group VIA and Group VIII metals and a non-acidic crystalline microporous material, wherein the amount of metal in the first catalyst is in the range of from about 0.05 to about 10 weight percent, at a temperature in the range of from about 300° to about 700° C. to form a first-stage product effluent;
    passing the first-stage product effluent over a second-stage catalyst bed maintained under a second set of conditions in which the temperature is less than about 300° C., wherein the second-stage catalyst bed comprises a second catalyst comprising palladium and a non-acidic crystalline microporous material, wherein the amount of palladium in the catalyst is in the range of from about 0.05 to about 10 weight percent; and recovering said cyclopentene-enriched product.

19. The process of claim 18, wherein the non-acidic crystalline microporous material exhibits the X-ray diffraction pattern of a zeolite selected from the group consisting of a zeolite having the structure of ZSM-5, ZSM-11, ZSM-12, ZSM-22, ZSM-23, ZSM-35, MCM-22, and PSH-3.

20. The process of claim 19, wherein the zeolite has the structure of ZSM-5 or MCM-22.

21. The process of claim 20, wherein the zeolite has the structure of ZSM-5.

22. The process of claim 21, wherein said zeolite having the structure of ZSM-5 contains a modifier comprising tin.

23. The process of claim 18, wherein said Group VIII metal is platinum.

24. The process of claim 18, which further includes cofeeding an inert diluent with said n-pentane.

25. The process of claim 24, wherein said diluent is nitrogen, methane or aromatic compounds, and admixtures thereof.

26. The process of claim 25, wherein the diluent is selected from the group consisting of $C_6$–$C_8$ aromatics and admixtures thereof.

27. A process for converting n-pentane to cyclopentene comprising:

contacting n-pentane with a first-stage catalyst bed in which the first catalyst comprises a Group VIA or Group VIII metal and a non-acidic microporous material, wherein the amount of Group VIA or Group VIII metal in the first catalyst is in the range of from about 0.05 to 10 weight percent, at a temperature in the range of from about 300° to about 700° C. to form a first-stage product effluent;

passing the first-stage product effluent over a second-stage catalyst bed maintained under a second set of conditions in which the temperature is in the range of from about 200° to about 300° C. wherein the second-stage catalyst bed comprises palladium and a non-acidic microporous material, wherein the amount of palladium in the second catalyst is in the range of from about 0.05 to about 10 weight percent; and recovering a second-stage product which comprises cyclopentene.

* * * * *